United States Patent [19]
Stanton

[11] Patent Number: 5,414,257
[45] Date of Patent: May 9, 1995

[54] MOISTURE SENSOR FOR DETECTING MOISTURE ON A WINDSHIELD

[75] Inventor: Peter R. Stanton, North Manly, Australia

[73] Assignee: Introlab Pty Limited, North Manly, Australia

[21] Appl. No.: 133,120

[22] PCT Filed: Apr. 23, 1992

[86] PCT No.: PCT/AU92/00183

§ 371 Date: Oct. 19, 1993

§ 102(e) Date: Oct. 19, 1993

[87] PCT Pub. No.: WO92/18848

PCT Pub. Date: Oct. 29, 1992

[30] Foreign Application Priority Data

Apr. 23, 1991 [AU] Australia .............................. PK5736

[51] Int. Cl.⁶ .......................... H01J 5/16; H01J 40/14
[52] U.S. Cl. ......................... 250/227.25; 318/DIG. 2
[58] Field of Search ................. 250/239, 227.25, 574; 340/602; 318/483, 444, DIG. 2

[56] References Cited

U.S. PATENT DOCUMENTS

| | | | |
|---|---|---|---|
| 3,458,889 | 8/1969 | Tann | 15/250.12 |
| 4,620,141 | 10/1986 | McCumber et al. | 318/483 |
| 4,676,638 | 6/1987 | Yasuda | 356/237 |
| 4,798,956 | 1/1989 | Hochstein | 250/341 |
| 4,871,917 | 10/1989 | O'Farrell et al. | 250/341 |
| 4,960,996 | 10/1990 | Hochstein | 250/349 |
| 4,973,844 | 11/1990 | O'Farrell et al. | 250/341 |
| 5,262,640 | 11/1993 | Purris et al. | 250/227.25 |

FOREIGN PATENT DOCUMENTS

0311005A2 10/1988 European Pat. Off. .
0444520A2 2/1991 European Pat. Off. .
3823300C1 8/1989 Germany .

OTHER PUBLICATIONS

Abstract of Japanese Patent Publication No. 59-8925-0(A), "Liquid Detector For Automatic Windshield Wiper Controller", May 23, 1984.
Abstract of Japanese Patent Publication No. 59-8594-4(A), "Liquid Detector For Automatic Wind Shield Wiper Controller Device", May 18, 1984.
Abstract of Japanese Patent Publication No. 59-15905-3(A), "Liquid Detector for Automatic Windshield Wiper Control Apparatus", Sep. 8, 1984.
Abstract of Australian Patent Specification No. Au-A-1-51,186/79, "Detecting Dust or Water on Vehicle Windscreen", Sep. 25, 1978.
Abstract of Japanese Patent Publication No. 59-100034, "Automatic Wiper Apparatus", Jun. 9, 1984.
Abstract of Japanes Patent Publication No. 59-57050, "Automatic Defrosting Control Device", Apr. 2, 1984.

Primary Examiner—David C. Nelms
Assistant Examiner—Steven L. Nichols
Attorney, Agent, or Firm—Nikaido, Marmelstein, Murray & Oram

[57] ABSTRACT

A moisture sensor device for a vehicle windshield consists of a housing having a front portion composed of transparent material forming a window with an inner surface formed in a stepwise shape with two planar surfaces oblique to the outer front surface and an outer surface of which is adapted to be optically coupled to an inner surface of the windshield. An internal body portion fits within the housing and has a stepwise shaped outer surface fitting to the inside surface of the window, and includes a radiant energy emitter and a radiant energy detector positioned at oblique surfaces complementary to those of the window. Radiant energy passes from the emitter to the detector through the window and windscreen optically coupled thereto in an optical path that includes internal reflections at an outer surface of the windshield and at a planer side surface of the window. A circuit board alongside the internal body includes circuitry for operating the sensor device.

9 Claims, 1 Drawing Sheet

MOISTURE SENSOR FOR DETECTING MOISTURE ON A WINDSHIELD

BACKGROUND ART

There are instances when it is necessary to determine moisture levels on a surface such as the windscreen or windshield of a vehicle.

In the case of the windscreens of road vehicles, there has been a number of attempts in the past to determine the need to wipe the windscreen by determining the current level of rainfall or the current level of water on the windscreen. Some of these attempts, such as is described in U.S. Pat. No. 4,355,271 (Noack), have used devices which emit radiant energy from the inside of the windscreen, and direct it at the outside windscreen surface at an angle such that it will be substantially totally internally reflected from a dry screen but allowed to substantially entirely pass through a wet screen. By suitably positioning a detector that will respond to the radiant energy, it can be determined whether or not the screen is wet. However, typical examples of such devices are inefficient due to reflective losses incurred when the radiant energy beam enters and leaves the windscreen at the inside air/screen interface at a similar angle. U.S. Pat. No. 4,620,141 (McCumber et al) discloses a sensor unit of this general type but further including a light conducting rod for each emitter and detector and may overcome the problem of reflective losses. Such devices tend to be less than straight forward to manufacture and assemble. Furthermore, the required physical dimensions of the prior art devices are inconveniently large in order to obtain the required relative location of the sensor and emitter.

DISCLOSURE OF THE INVENTION

The present invention seeks to overcome the disadvantages in the prior art by providing a device which will be more easily manufactured and assembled and of compact size.

The invention provides a moisture sensor which is formed in a compact arrangement that lends itself to ready repair or replacement of its active components without removal of the entire unit from a fixed position on the interior of a windscreen and so offers a desirable alternative to existing sensor arrangements. In one embodiment the sensor provides a device to be optically coupled to the inside of a windscreen and which utilizes a radiant energy path within a transparent window, the path initially entering and finally leaving the window perpendicularly to surfaces provided for that purpose, and the proportion of radiant energy being internally reflected from the outside windscreen surface being indicative of its degree of dryness. When the outside surface is wet substantial radiant energy is transmitted through the surface and the detected signal reduced; when dry substantially total internal reflection occurs. Accordingly, throughout this specification, the terms wet and dry indicate the presence or absence of water, ice, or the like substance that will change the optical path of the radiant energy at that outside surface.

Accordingly, in one broad form, the present invention provides a moisture sensor comprising a housing incorporating window means, said window means being composed of material transparent to radiant energy from a radiant energy emitter and having at least one outermost front surface adapted to be optically coupled to an inside surface of a windscreen, a body means incorporating said emitter and a sensor for sensing radiant energy emitted by said emitter, said body means being of a stepwise shape which is a slide fit within the housing in the direction of the step so as to fit against a complementary innermost surface of said window means, and wherein said innermost surface of said window means comprises an emitter surface and a sensor surface.

Preferably the window means is a one piece window and the front surface means is a continuous front surface.

Preferably the emitter is an infra-red diode.

Preferably the window means includes a further surface positioned along the radiant energy path and providing a surface of total internal reflection to the radiant energy. It is further preferred that this further surface be intermediate the emitter surface and the front surface.

It is preferred that the radiant energy path is such that the angle of incidence with the front surface is preselected within an angle range being dependent upon the frequency of radiant energy to be used and the refractive index of the material in which the window is produced such that the radiant energy will be totally internally reflected by the front surface when the outside front surface interfaces with air, i.e. the surface is dry.

BEST MODE OF CARRYING OUT INVENTION

Figure 1:
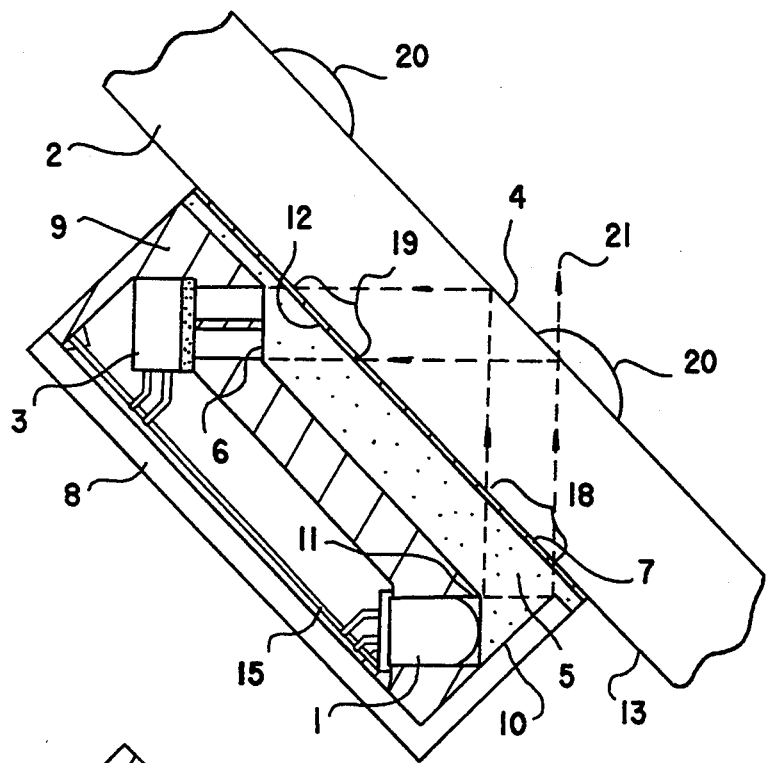
FIG. 1 is a cross-sectional view of an embodiment of the invention attached operatively to the inside of a vehicle windscreen.

FIG. 1 shows a typical installation for use in a car, or other road vehicle. However, the installation could equally well be incorporated in any other type of vehicle which includes a windscreen and a windscreen wiping system similar of those commonly found on road vehicles.

The device includes a general housing 8 wholly composed of plastics material having a front opening covered by a window 5 which is substantially transparent to infrared energy to form an integral part of the housing 8. The window 5 is fixed to the inside surface 13 of a vehicle windscreen 2 by a clear layer of adhesive 7, or similar, and may form a permanently contiguous bond such that the window 5 and windscreen 2 become effectively an integral structure. The clear adhesive 7 acts to optically couple the window 5 to the windscreen 2. The entire surface adhered to the windscreen is transparent which reduces the obviousness of the device to an outside observer.

An internal body 9 anchors at least one infra-red emitting diode 1, a corresponding at least one sensor 3 and a circuit board 15 providing electronic support.

For operational purposes the adhesive layer 7 may be replaced by any non-adhesive optical coupling layer, such as petroleum jelly, and some alternative means provided in order to fix the device in position relative to the windscreen 2.

The window 5 may be produced in two parts, separated along a line between the portions 18 and 19 being the exit and entry portions of the radiant energy however the one piece construction illustrated is preferable.

The window 5 includes an emitter radiant energy receiving surface 11 proximate to the emitter 1 and a side surface 10 approximately perpendicular to a front surface 12 of the window 5. Proximate the sensor 3 is a sensor radiant energy receiving surface 6 lying parallel to the emitter surface 11. The emitter 1 and sensor 3 are positioned perpendicular to their respective surfaces 11 and 6.

It should be noted that operatively, the relative angles of the surfaces 6, 10, 11 and 12 may be altered but it is preferred that the surfaces 11 and 6 are obliquely angled to the same side of a perpendicular to the front surface, as discussed later, and the radiant energy path remains primarily as described further in this specification. The general arrangement illustrated and described in detail provides a physically compact device which is easily assembled.

The electrical hardware supporting the device is held on circuit board 15 and includes an electrical supply for the infra-red emitting diode 1 and signal receiving circuits connected to the infra-red sensor 3. It is connected to other vehicle electrics by wires not shown in the drawings.

In operation infra-red energy emitted from emitter 1 passes perpendicularly through the emitter surface 11 and is totally internally reflected from the side surface 10 thence passes substantially straight through the optically coupled interface between the front surface 12 at portion 18 and into the windscreen 2. At the outside surface 4 of the windscreen 2, total internal reflection of the infra-red energy will occur if the surface 4 is substantially dry. If the surface 4 is partially wet by water drops 20 then the infra-red energy will be proportionately transmitted through the outside surface 4 as energy 21 and the sensor 3 will receive a proportionately diminished signal.

The totally internally reflected portion of infra-red beam passes through the optically coupled interface between the window 5 and the windscreen 2 at portion 19, finally leaving the window 5 perpendicularly through the sensor surface 6 so as to strike and affect the sensor 3. The sensor 3 is used to produce a signal detected and processed by the connected electronics proportional to the dryness of the windscreen 2.

The optical coupling of the window 5 and windscreen 2 and the infra-red energy entering and leaving perpendicularly to the sensor and emitter surfaces allows the device to operate in a most efficient manner in that there can be virtually no losses of radiant energy due to significant unwanted reflection. Furthermore, the emitter and sensor devices can be positioned close to one another and in parallel alignment so as to provide a compact assembly.

Figure 2:
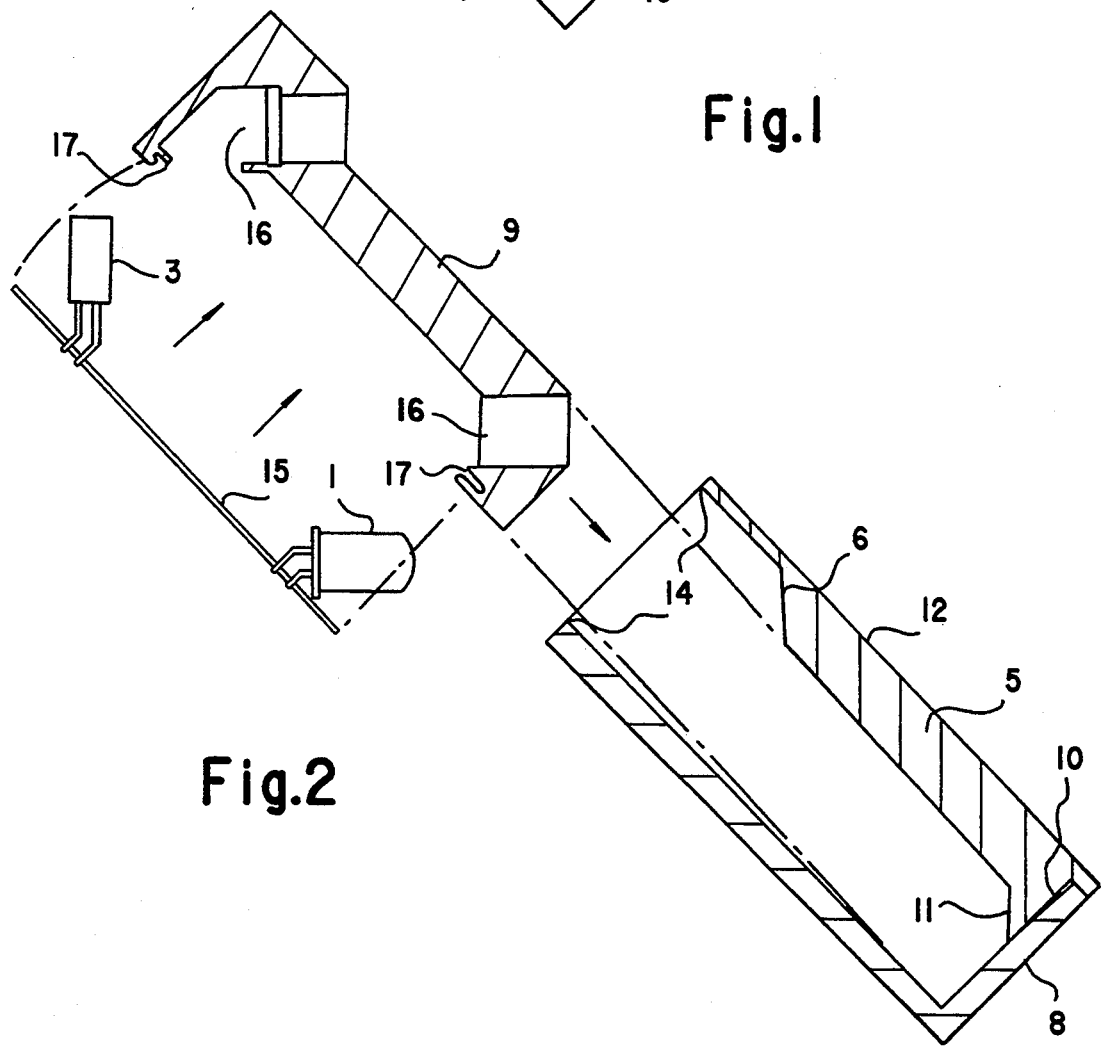
FIG. 2 is a cross-sectional view of a disassembled moisture sensor in accordance with the invention.

FIG. 2 shows the moisture sensor device in a disassembled state.

The circuit board 15 includes the emitter 1 and sensor 3 soldered into place and preangled so as to coincide with their intended operational directions. The board 15 is then positioned behind the body 9, on the side opposite the side which will be adjacent the window 5. As the board 15 is brought up into position relative to the body 9 the emitter 1 and sensor 3 will align with and enter their respective holes 16 which will finally anchor those components in position. Finally, the board 15 enters the attachments 17 to hold the board 15 in place.

Next, the sub-assembly comprising the board 15, the body 9, the emitter 1 and the sensor 3, is slid into the hollow interior of the housing 8 which itself already includes the transparent window 5. With the angle of the emitter surface 11 and the sensor surface 6 being both on the same side of a perpendicular to the front face 12, that is they are in a common 90° arc drawn from the front surface 12, the body 9 easily self aligns and positions within the hollow relative to the rear surface of the window 5 being finally held in position by detents 14.

Thus the major components can all be injection molded and are very easily assembled so as to be inexpensively produced. Further, as the electrical components attached to the board 15 can be quickly detached from the housing 8 which is adhered via the window 5 to the windscreen 2, an electrical fault or a broken windscreen can easily be remedied without necessitating the replacement of the operational part of the sensor. Also, as the body 9 is slid into the housing 8 in a direction parallel to the front face 12, it is very easily inserted into the housing 8, after it has been fixed to a windscreen 2 and installed in a vehicle, from above with gravity then assisting to maintain the components in their correct place and the length of the electrical wiring being minimal.

I claim:

1. A moisture sensor comprising:
  a housing and an internal body fitting within said housing;
  a window means on a front portion of said housing composed of a material transparent to radiant energy and having an outer front surface adapted to be optically coupled to an inside surface of a windscreen;
  said window means having an inner surface formed in a stepwise shape with a first planar surface oblique to said outer front surface, a second surface extending from said first surface substantially parallel to said outer front surface, an oblique third planar surface extending from said second surface, and a planar side surface adjacent said oblique third planar surface, and;
  said internal body having a front outer surface of a stepwise shape fitting to said inner surface of said window means, and having a radiant energy emitter with an emitter surface positioned at an oblique surface complementary to one of said window means oblique surfaces and a radiant energy sensor means positioned at another oblique surface complementary to the other of said window means oblique surfaces;
  such that when said internal body is fitted into said housing said window means provides an optical path between said radiant energy emitter means and said radiant energy sensor means passing internally through said window means and a windscreen optically coupled thereto, said optical path including internal reflections at an outer surface of said windscreen and at said planar side surface of said window means.

2. A moisture sensor as defined in claim 1 wherein the window means is a single piece window and the front surface is a continuous surface.

3. A moisture sensor as defined in claim 1 wherein said window means front surface is adhered and optically coupled to the inside surface of the windscreen by adhesive substantially transparent to the emitter radiant energy.

4. A moisture sensor as claimed in claim 1 wherein the window means is composed substantially entirely of plastics material and the oblique surfaces are angled to said front surface at between 30° and 60°, and said side surface is substantially perpendicular to said front surface, and said oblique surfaces, side surface and front surface all being substantially perpendicular to a plane of said optical path and further said side surface being intersected by an imaginary line extending substantially perpendicularly from one of the oblique surfaces.

5. A moisture sensor as defined in claim 4 wherein said oblique surfaces are angled at about 45° to said front surface.

6. A moisture sensor as claimed in claim 1 wherein
said internal body positions the emitter proximate and aligned with one oblique surface to provide radiant energy directed substantially perpendicularly into the window means through said surface and positions the sensor proximate and aligned with the other oblique surface to receive radiant energy directed substantially perpendicularly out through said surface,
said window means being configured to provide a radiant energy path, when optically coupled to the inside surface of a windscreen, from said emitter to the outside surface of the windscreen to be internally reflected at the outside surface of the windscreen, to a degree proportional to the dryness of said outside surface, and the reflected portion of the radiant energy to proceed to and exit said window means substantially perpendicularly to said sensor.

7. A moisture sensor as defined in claim 1 wherein said internal body includes an electronic board including electronic circuitry means for supporting the operation of the emitter and the sensor.

8. A moisture sensor as defined in claim 6 wherein the emitter is an infra-red emitting diode.

9. A moisture sensor as defined in claim 1 further including a circuit board to which said emitter and said sensor are fixed and wherein said circuit board is positioned and held alongside said internal body on a side of said body opposite said window means, and wherein said body includes holes for locating said emitter and said sensor, and during positioning of said circuit board to be held alongside said body said emitter and said sensor are self aligned with and enter respective holes in said body.

* * * * *